United States Patent
Lee et al.

(10) Patent No.: US 9,724,486 B2
(45) Date of Patent: Aug. 8, 2017

(54) IN-EXSUFFLATION THERAPY AUTO-ADJUSTMENT

(71) Applicant: KONINKLIJKE PHILIPS N.V., Eindhoven (NL)

(72) Inventors: Seunghyun Lee, Murrysville, PA (US); April Stewart Nathan, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 249 days.

(21) Appl. No.: 14/405,046

(22) PCT Filed: May 24, 2013

(86) PCT No.: PCT/IB2013/054289
§ 371 (c)(1),
(2) Date: Dec. 2, 2014

(87) PCT Pub. No.: WO2013/182944
PCT Pub. Date: Dec. 12, 2013

(65) Prior Publication Data
US 2015/0165144 A1    Jun. 18, 2015

Related U.S. Application Data

(60) Provisional application No. 61/655,546, filed on Jun. 5, 2012.

(51) Int. Cl.
*A61M 11/00* (2006.01)
*A61M 16/00* (2006.01)
(Continued)

(52) U.S. Cl.
CPC ........ *A61M 16/0069* (2014.02); *A61M 16/00* (2013.01); *A61M 16/0003* (2014.02);
(Continued)

(58) Field of Classification Search
CPC .......... A61M 16/0069; A61M 16/0666; A61M 16/20; A61M 16/0003; A61M 16/0009;
(Continued)

(56) References Cited

U.S. PATENT DOCUMENTS 4,977,889 A    12/1990 Budd
8,122,885 B2   2/2012 Berthon-Jones
(Continued)

FOREIGN PATENT DOCUMENTS

CN    102481426 A    5/2012
JP    2005193063 A   7/2005
(Continued)

*Primary Examiner* — Steven Douglas
(74) *Attorney, Agent, or Firm* — Michael W. Haas

(57) ABSTRACT

The present disclosure pertains to a method and system configured to in-exsufflate a subject by controlling the in-exsufflation pressure waveform. In some embodiments, the system comprises a pressure generator, a subject interface, one or more sensors, one or more processors, electronic storage, a user interface, and/or other components. The system is configured to assist the subject to loosen and/or expel secretions by inducing a percussive pressure waveform delivered to the subject during inhalation and/or exhalation. The system is configured to control the in-exsufflation therapy delivered to the subject without requiring regular manual setting and/or adjustment of pressures, pressure amplitudes, a frequency range, and/or other parameters of the percussive pressure waveform.

15 Claims, 4 Drawing Sheets

(51) Int. Cl.
*A61M 16/06* (2006.01)
*A61M 16/20* (2006.01)
*A61B 5/00* (2006.01)
*A61B 5/087* (2006.01)

(52) U.S. Cl.
CPC .... *A61M 16/0006* (2014.02); *A61M 16/0009* (2014.02); *A61M 16/0666* (2013.01); *A61M 16/20* (2013.01); *A61B 5/087* (2013.01); *A61B 5/4848* (2013.01); *A61M 2016/003* (2013.01); *A61M 2016/0033* (2013.01); *A61M 2205/3317* (2013.01); *A61M 2205/3334* (2013.01); *A61M 2205/3365* (2013.01); *A61M 2205/50* (2013.01); *A61M 2205/502* (2013.01); *A61M 2205/70* (2013.01)

(58) Field of Classification Search
CPC .............. A61M 16/0006; A61M 16/00; A61M 2205/70; A61M 2205/502; A61M 2205/3334; A61M 2016/003; A61M 2205/50; A61M 2205/3365; A61M 2205/3317; A61M 2016/0033; A61B 5/087; A61B 5/4848
See application file for complete search history.

(56) References Cited

U.S. PATENT DOCUMENTS

| | | |
|---|---|---|
| 2005/0051174 A1 | 3/2005 | Emerson |
| 2008/0000477 A1 | 1/2008 | Huster |
| 2009/0007913 A1 | 1/2009 | Lee |
| 2009/0126731 A1* | 5/2009 | Dunsmore ........ A61M 16/0096 128/203.12 |
| 2012/0111329 A1 | 5/2012 | Brand et al. |
| 2012/0285460 A1* | 11/2012 | Smith .................. A61M 16/20 128/205.24 |
| 2014/0150791 A1* | 6/2014 | Birnkrant .......... A61M 16/0006 128/204.23 |

FOREIGN PATENT DOCUMENTS

| | | |
|---|---|---|
| WO | WO2007106804 A2 | 9/2007 |
| WO | WO2010058308 A2 | 5/2010 |

\* cited by examiner

IN-EXSUFFLATION THERAPY AUTO-ADJUSTMENT

CROSS-REFERENCE TO RELATED APPLICATIONS

This patent application claims the priority benefit under 35 U.S.C. §371 of international patent application no. PCT/IB2013/054289, filed May 24, 2013, which claims the priority benefit under 35 U.S.C. §119(e) of U.S. Provisional Application No. 61/655,546 filed on Jun. 5, 2012, the contents of which are herein incorporated by reference.

BACKGROUND OF THE INVENTION

1. Field of the Invention

The present disclosure pertains to a method and system configured to in-exsufflate a subject by controlling the in-exsufflation pressure waveform provided to the subject.

2. Description of the Related Art

Various systems for increasing patient cough flow through in-exsufflation are known. Conventional exsufflation is generally accomplished using a single exsufflation event over a single exhalation of the subject. A respiratory circuit may be pressurized by the subject, and then the circuit may be opened once, while all (or substantially all) of the gas that pressurized the circuit is expelled therethrough. Secretions built up in the airway of the subject over time may be expelled with the gas. Control of the operation of systems used for in-exsufflation may include the user and/or care giver manually setting and/or adjusting one or more pressures and one or more time parameters related to the duration of inhalation, exhalation, or the pressure waveform. Patients and caregivers are required to manually set a patient and/or care giver perceived optimum in-exsufflation therapy level.

SUMMARY OF THE INVENTION

Accordingly, one or more aspects of the present disclosure relate to a system configured to in-exsufflate a subject. The system comprises a pressure generator, a subject interface, one or more sensors, and one or more processors. The pressure generator is configured to generate a flow of breathable gas for delivery to an airway of the subject according to an in-exsufflation therapy regime. The subject interface is configured to place the pressure generator in fluid communication with the airway of the subject. The one or more sensors are configured to generate one or more output signals conveying information related to one or more parameters of the flow of gas. The one or more processors are configured to execute computer program modules. The computer program modules comprise a control module, an effectiveness module, and an adjustment module. The control module is configured to control the pressure generator according to the in-exsufflation therapy regime. Controlling the pressure generator according to the in-exsufflation therapy regime comprises causing the pressure generator to modulate a gas pressure within a respiratory phase between two or more pressure levels to generate a percussive pressure waveform during the respiratory phase, and monitoring the responsiveness of a flow rate of the flow of breathable gas to the modulations in pressure during the respiratory phase. The effectiveness module is configured to determine the effectiveness of the in-exsufflation therapy regime. The determination of effectiveness is based on the responsiveness of the flow rate to the modulations in pressure. The adjustment module is configured to adjust one or more parameters of the percussive pressure waveform to enhance the responsiveness of the flow rate.

Yet another aspect of the present disclosure relates to a method to in-exsufflate a subject with an in-exsufflation system. The system comprises a pressure generator, a subject interface, one or more sensors, and one or more processors. The processor comprises a control module, an effectiveness module, and an adjustment module. The method comprises generating a flow of breathable gas for delivery to an airway of the subject according to an in-exsufflation therapy regime with the pressure generator; communicating the flow of breathable gas to the airway of the subject with the subject interface; generating output signals conveying information related to one or more gas parameters of the flow of breathable gas with the one or more sensors; executing computer program modules with the processor; controlling the pressure generator according to the in-exsufflation therapy regime with the control module, wherein controlling the pressure generator according to the in-exsufflation therapy regime comprises causing the pressure generator to modulate a gas pressure within a respiratory phase between two or more pressure levels to generate a percussive pressure waveform during the respiratory phase, and monitoring the responsiveness of a flow rate of the flow of breathable gas to the modulations in pressure during the respiratory phase; determining the effectiveness of the in-exsufflation therapy regime with the effectiveness module, the determination of effectiveness based on the responsiveness of the flow rate to the modulations in pressure; and adjusting one or more parameters of the percussive pressure waveform to enhance the responsiveness of the flow rate with the adjustment module.

Still another aspect of the present disclosure relates to a system configured to in-exsufflate a subject. The system comprises means for generating a flow of breathable gas for delivery to an airway of the subject according to an in-exsufflation therapy regime; means for communicating the flow of breathable gas to the airway of the subject; means for generating output signals conveying information related to one or more gas parameters of the flow of breathable gas; means for executing computer program modules; means for controlling the means for generating according to the in-exsufflation therapy regime, wherein controlling the means for generating according to the in-exsufflation therapy regime comprises causing the pressure generator to modulate a gas pressure within a respiratory phase between two or more pressure levels to generate a percussive pressure waveform during the respiratory phase, and monitoring the responsiveness of a flow rate of the flow of breathable gas to the modulations in pressure during the respiratory phase; means for determining the effectiveness of the in-exsufflation therapy regime, the determination of effectiveness based on the responsiveness of the flow rate to the modulations in pressure; and means for adjusting one or more parameters of the percussive pressure waveform to enhance the responsiveness of the flow rate.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the

DETAILED DESCRIPTION OF EXEMPLARY EMBODIMENTS

Figure 1:
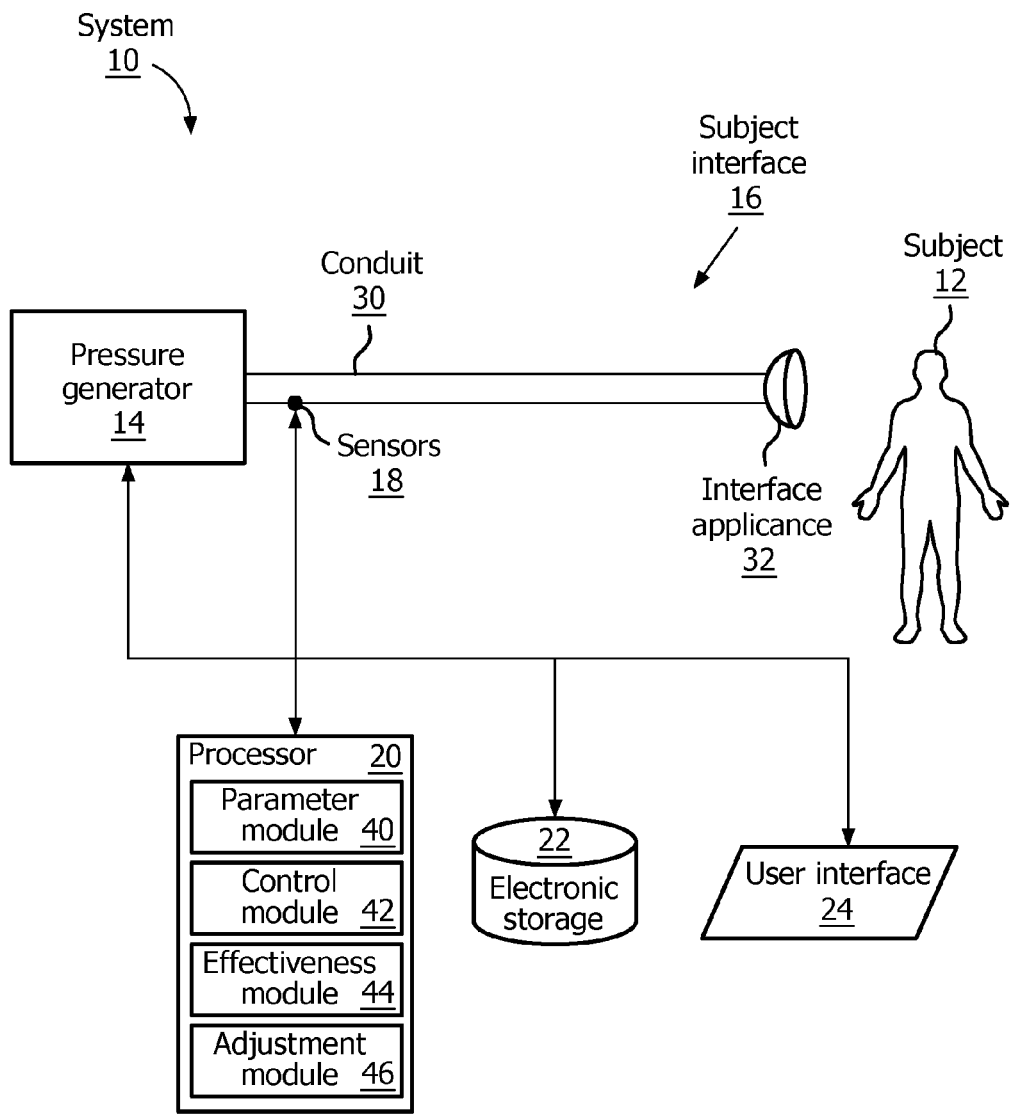
FIG. 1 schematically illustrates an exemplary embodiment of a system configured to in-exsufflate a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates an exemplary embodiment of a system 10 configured to in-exsufflate a subject 12. In some embodiments, system 10 comprises a pressure generator 14, a subject interface 16, one or more sensors 18, one or more processors 20, electronic storage 22, a user interface 24, and/or other components. System 10 is configured to assist subject 12 to loosen and/or expel secretions by inducing a percussive pressure waveform delivered to subject 12 during inhalation and/or exhalation. System 10 is configured to control the in-exsufflation therapy delivered to subject 12 without requiring regular manual setting and/or adjustment of pressures, pressure amplitudes, a frequency range, and/or other parameters of the percussive pressure waveform.

Pressure generator 14 is configured to provide a pressurized flow of breathable gas for delivery to the airway of subject 12 according to an in-exsufflation therapy regime. Pressure generator 14 receives a flow of gas from a gas source, such as the ambient atmosphere, and elevates the pressure of that gas for delivery to subject 12. In some embodiments, pressure generator 14 is configured to generate negative pressure to draw gas from subject 12. Pressure generator 14 is configured to modulate the pressure and/or frequency of the pressurized flow of breathable gas in accordance with the in-exsufflation therapy regime. In some embodiments, pressure generator 14 is a device dedicated to inexsufflation. In some embodiments, pressure generator 14 is a ventilator and/or positive airway pressure device configured to provide therapy other than and/or in addition to inexsufflation. Pressure generator 14 may be configured such that one or more gas parameters of the pressurized flow of breathable gas in addition to and/or other than pressure are controlled in accordance with the therapy regime. The one or more gas parameters may include, for example, one or more of volume, flow rate, temperature, gas composition, velocity, acceleration, and/or other parameters.

In some embodiments, pressure generator 14 may include any device, such as, for example, a pump, blower, piston, or bellows, that is capable of elevating the pressure of the received gas for delivery to a patient. In some embodiments, pressure generator 14 may include one or more devices, such as for example, a valve and/or a series of valves, capable of controlling the pressure, flow rate, flow direction, oscillation frequency, and/or other parameters of the flow of gas. The present disclosure contemplates controlling the operating speed of the blower, for example, either alone or in combination with one or more valves and/or other devices contained in and/or external to pressure generator 14, to control the pressure and/or flow of gas provided to subject 12. For example, pressure generator 14 may selectively control the flow direction of the flow of gas such that pressure levels during exsufflation may be negative according to the in-exsufflation therapy regime. The present disclosure contemplates that gas other than ambient atmospheric air may be introduced into system 10 for delivery to the patient.

Subject interface 16 is configured to interface with the airway of subject 12. Subject interface 16 is configured to provide fluid communication between pressure generator 14 and the airway of subject 12. As such, subject interface 16 comprises a conduit 30, an interface appliance 32, and/or other components. Conduit 30 is configured to form a flow path through which the pressurized flow of breathable gas is communicated between pressure generator 14 and interface appliance 32. Conduit 30 may be a flexible length of hose, or other conduit, that places interface appliance 32 in fluid communication with pressure generator 14. Conduit 30 conveys gas (e.g., air) to and/or from interface appliance 32, and interface appliance 32 places conduit 30 in communication with the airway of subject 12. In some embodiments, interface appliance 32 is non-invasive. As such, interface appliance 32 non-invasively engages subject 12. Non-invasive engagement includes removably engaging an area (or areas) surrounding one or more external orifices of the airway of subject 12 (e.g., nostrils and/or mouth) to communicate gas between the airway of subject 12 and subject interface 16. Some examples of non-invasive interface appliance 32 may include, for example, a blow tube, a nasal cannula, a nasal mask, a nasal/oral mask, a full face mask, a total face mask, or other interface appliances that communicate a flow of gas with an airway of a subject.

Sensors 18 are configured to generate output signals conveying information related to one or more gas parameters of the gas within subject interface 16. The one or more gas parameters may comprise flow rate, pressure, volume, temperature, humidity, velocity, and/or other gas parameters. Sensors 18 may comprise one or more sensors that measure such parameters directly (e.g., through fluid communication with the flow of gas in subject interface 16). Sensors 18 may comprise one or more sensors that generate output signals related to one or more parameters of the flow of gas indirectly. By way of a non-limiting example, one or more of sensors 18 may generate an output based on an operating parameter of the pressure generator 14 (e.g., a motor current, voltage, rotational velocity, and/or other operating parameters), and/or other sensors. Although sensors 18 are illustrated at a single location within (or in communication with) conduit 30 between interface appliance 32 and pressure generator 14, this is not intended to be limiting. Sensors 18 may include sensors disposed in a plurality of locations, such as for example, within pressure generator 14, within (or in communication with) interface appliance 32, and/or other locations.

Processor 20 is configured to provide information processing capabilities in system 10. As such, processor 20 may include one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 includes a plurality of processing units. These processing units may be physically located within the same device, or processor 20 may represent processing functionality of a plurality of devices operating in coordination.

As shown in FIG. 1, processor 20 may be configured to execute one or more computer program modules. The one or more computer program modules comprise one or more of a parameter module 40, a control module 42, an effectiveness module 44, an adjustment module 46, and/or other modules. Processor 20 may be configured to execute modules 40, 42, 44, and/or 46 by software; hardware; firmware; some combination of software, hardware, and/or firmware; and/or other mechanisms for configuring processing capabilities on processor 20.

It should be appreciated that although modules 40, 42, 44 and 46 are illustrated in FIG. 1 as being co-located within a single processing unit, in implementations in which processor 20 includes multiple processing units, one or more of modules 40, 42, 44, and/or 46 may be located remotely from the other modules. The description of the functionality provided by the different modules 40, 42, 44, and/or 46 described below is for illustrative purposes, and is not intended to be limiting, as any of modules 40, 42, 44, and/or 46 may provide more or less functionality than is described. For example, one or more of modules 40, 42, 44, and/or 46 may be eliminated, and some or all of its functionality may be provided by other ones of modules 40, 42, 44, and/or 46. As another example, processor 20 may be configured to execute one or more additional modules that may perform some or all of the functionality attributed below to one of modules 40, 42, 44, and/or 46.

Parameter module 40 is configured to determine one or more parameters within system 10. The one or more parameters within system 10 may comprise gas parameters related to the pressurized flow of breathable gas, breathing parameters related to the respiration of subject 12 and/or other parameters. Parameter module 40 is configured to determine the one or more parameters based on the output signals of sensors 18, and/or other information. The information determined by parameter module 40 may be used for controlling pressure generator 14, stored in electronic storage 24, displayed by user interface 24, and/or used for other uses. The one or more parameters determined by parameter module 40 may comprise, for example, one or more of a flow rate, pressure, a volume, humidity, temperature, acceleration, velocity, respiration rate, tidal volume, and/or other parameters.

Control module 42 is configured to control pressure generator 14 to generate the flow of gas in accordance with the in-exsufflation therapy regime. Control module 42 is configured to control pressure generator 14 based on information related to the output signals from sensors 18, information determined by parameter module 40, information entered by a user to user interface 24, and/or other information.

Control module 42 is configured to control pressure generator 14 to modulate the pressure of the pressurized flow of breathable gas within a respiratory phase (inhalation or exhalation) to generate a percussive pressure waveform. Modulation of the pressure may comprise alternating the pressure delivered to subject 12 between two or more pressure levels within a respiratory phase, and/or controlling the frequency of pressure alternation. Control module 42 may be configured to cause pressure generator 14 to alternate pressure levels around a first local median pressure with a first amplitude during an inhalation of subject 12, and around a second local median pressure with a second amplitude during an exhalation of subject 12. The second local median pressure may be lower than the first median pressure. The second local median pressure and/or the alternating pressures around the second local median pressure may be negative pressures. Control module 42 is configured to control pressure generator 14 to reduce the median pressure of the pressurized flow of breathable gas for exsufflation compared to insufflation with sufficient abruptness that expiratory flow through the airway of the subject is sufficient to remove mucus and/or other debris from the airway and/or lungs of the subject. The first amplitude and the second amplitude may be the same.

Figure 2:
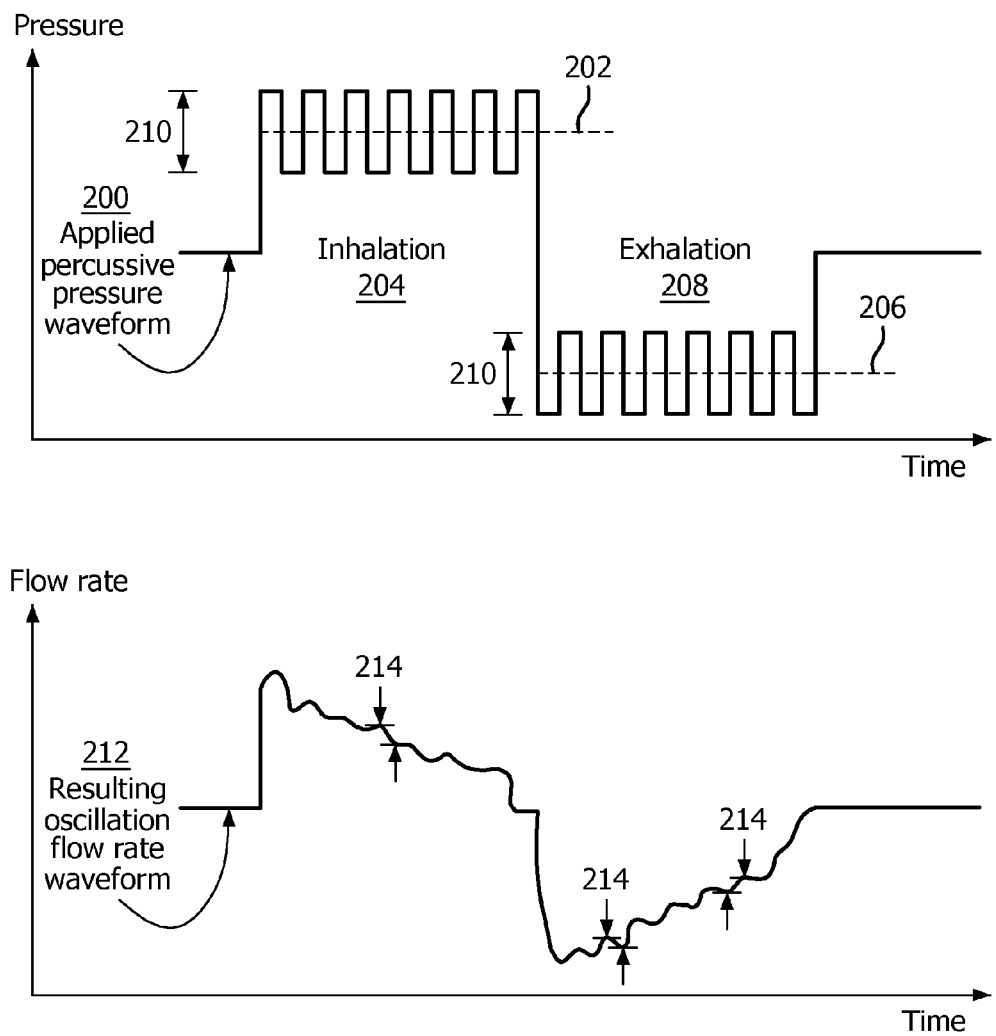
FIG. 2 shows an example of an applied percussive pressure waveform and the resulting oscillating flow rate waveform.

By way of a non-limiting example, FIG. 2 shows an applied percussive pressure waveform 200. Applied percussive pressure waveform 200 has a local median pressure 202 of about 37.5 cm $H_2O$ during inhalation 204, a local median pressure 206 of about negative 37.5 cm $H_2O$ during exhalation 208, an amplitude 210 of 5 cm $H_2O$, and a frequency of 10 Hz. In example FIG. 2 local median pressure 206 during exhalation is lower than local median pressure 204 during inhalation and the transition between the two is abrupt.

Returning to FIG. 1, control module 42 is configured to determine initial percussive pressure waveform parameters (e.g., an initial first local median pressure, second local median pressure, amplitude, oscillation frequency) such that control module 42 may control pressure generator 14 to begin in-exsufflation therapy at the determined initial percussive pressure waveform parameters. Initial percussive pressure waveform parameters may be determined at manufacture, determined from information entered by a user via user interface 24, determined from previous respiration by subject 12, determined from information related to previous in-exsufflation therapy on subject 12, and/or determined by another method. From the initial starting amplitude, control module 42 is configured to ramp the percussive pressure waveform amplitude to a maximum amplitude over one or more respiratory phases. In some embodiments the maximum amplitude may be about 15 cm of water. In some embodiments, the maximum amplitude may be about 10 cm of water. In some embodiments, the maximum amplitude may be about 5 cm of water.

Control module 42 is configured to monitor the responsiveness of the flow rate of the flow of breathable gas to the applied modulations in pressure during the respiratory phase. Control module 42 is configured to monitor the responsiveness of the flow rate based on information related to the output signals from sensors 18, information determined by parameter module 40, and/or other information.

By way of a non-limiting example, the in-exsufflation therapy regime may dictate that the percussive pressure waveform is delivered to the airway of subject 12 starting at a first local median pressure during inhalation (e.g., 40 cm $H_2O$), a second local median pressure during exhalation (e.g., 10 cm $H_2O$), an initial amplitude (e.g., 5 cm $H_2O$), and an initial frequency (e.g., 10 Hz). Control module 42 may control pressure generator 14 to steadily increase the amplitude of the waveform up to 10 cm of water during a series of inhalations and exhalations by subject 12.

In some embodiments, control module 42 may control pressure generator 14 such that the pressure support provided to the subject via the flow of gas comprises therapy in addition to inexsufflation. Therapy in addition to and/or instead of in-exsufflation may comprise, for example, continuous positive airway pressure support (CPAP), bi-level positive airway pressure support (BPAP), proportional positive airway pressure support (PPAP), and/or other types of pressure support therapy.

Effectiveness module 44 is configured to determine the effectiveness of the in-exsufflation therapy regime. The determination of effectiveness is based on the responsiveness of the flow rate to the modulations in pressure. In some embodiments, effectiveness of the in-exsufflation therapy regime may be determined based on information related to a parameter other than flow rate. Information related to the responsiveness of the flow rate may be determined based on information related to the output signals from sensors 18, information determined by parameter module 40, information determined by control module 42, and/or other information. Increased responsiveness of the flow rate to the modulations in pressure indicates increased effectiveness. Increased oscillating flow rate amplitude indicates greater responsiveness.

Revisiting the example in FIG. 2, a resulting oscillating flow rate waveform 212 is monitored after generation of applied percussive pressure waveform 200. Resulting oscillating flow rate waveform 212 has a variable amplitude 214. Variable amplitude 214 is an indication of the responsiveness of the flow rate to the modulations in pressure. Increasing amplitude 214 indicates greater responsiveness.

Returning to FIG. 1, effectiveness module 44 may be configured to determine the effectiveness of the in-exsufflation therapy regime one or more times during a respiratory phase. In some embodiments, effectiveness module 44 may determine the effectiveness of the in-exsufflation therapy regime for one or more respiratory phases in a series of respiratory phases. In some embodiments, effectiveness module 44 may determine the effectiveness of the in-exsufflation therapy regime for one or more series of respirations by subject 12. Effectiveness module 44 may determine the effectiveness of the in-exsufflation therapy regime responsive to the initial application of in-exsufflation therapy by control module 42 and/or adjustments to the percussive pressure waveform made by adjustment module 46.

In some embodiments, effectiveness module 44 determines the oscillating flow rate amplitude after each pressure modulation. In some embodiments effectiveness module 44 may determine a flow rate amplitude after one or more pressure oscillations in a series of pressure oscillations (e.g., average flow rate amplitude). In some embodiments, effectiveness module 44 may determine a flow rate amplitude representative of the flow rate amplitude during inhalation (e.g., average flow rate amplitude during inhalation), and a flow rate amplitude representative of the flow rate amplitude during exhalation (e.g., average flow rate amplitude during exhalation.)

Effectiveness module 44 is configured to determine an effectiveness threshold. Effectiveness module 44 is configured to compare the information indicating effectiveness (e.g., the amplitude of the oscillating flow rate) to the effectiveness threshold. Effectiveness module 42 is configured to determine that the in-exsufflation therapy regime is effective and/or ineffective based on the information indicating effectiveness relative to the effectiveness threshold. By way of a non-limiting example, when the amplitude of the oscillating flow rate breaches the effectiveness threshold, effectiveness module 44 may determine that the in-exsufflation therapy regime is effective. When the amplitude of the oscillating flow rate does not breach the effectiveness threshold, effectiveness module 44 may determine that the in-exsufflation therapy regime is ineffective. The effectiveness threshold may be configurable to a user (e.g., subject 12, a doctor, a caregiver, a researcher, and/or other users) through user interface 24, determined at manufacture, determined based on previous respiration by subject 12, determined based on information related to previous in-exsufflation therapy administered to subject 12, and/or determined by other methods.

Adjustment module 46 is configured to adjust one or more parameters of the percussive pressure waveform to enhance the responsiveness of the flow rate of the flow of breathable gas. Adjustment module 46 is configured to adjust the one or more parameters of the percussive pressure waveform responsive to a determination by effectiveness module 44 that the in-exsufflation therapy regime is not effective. Responsive to the determination that the in-exsufflation therapy regime is not effective, adjustment module 46 is configured to control pressure generator 14 to sweep the percussive pressure waveform through one or more frequencies in a frequency range. The frequency range may be determined at manufacture, determined from information entered by a user via user interface 24, determined from previous respiration by subject 12, determined from information related to previous in-exsufflation therapy on subject 12, and/or determined by another method. Adjustment module 46 is configured to stop sweeping the percussive pressure waveform through the one or more frequencies in the frequency range responsive to a determination by effectiveness module 44 that the in-exsufflation therapy regime is effective, and/or when one or more limits of the frequency range are reached.

In some embodiments, adjustment module 46 may be configured to adjust the local median pressures, the amplitude, and/or other parameters of the percussive pressure waveform in addition to and/or instead of the frequency. In some embodiments, adjustment module 46 may be configured to optimize the parameters of the percussive pressure waveform (e.g., pressure, amplitude, frequency) to achieve a maximum oscillating flow rate amplitude. Adjustment module 46 may be configured to optimize the parameters of the percussive pressure waveform to achieve a maximum oscillating flow rate amplitude in an ongoing manner during an in-exsufflation therapy session. In some embodiments, adjustment module 46 may be configured to adjust one or more parameters of the percussive waveform differently for inhalation compared to exhalation.

As introduced above, FIG. 2 shows applied percussive pressure waveform 200 and resulting oscillating flow rate waveform 212. FIG. 2 may represent the initial in-exsufflation therapy percussive pressure waveform generated by a pressure generator (e.g., pressure generator 14 shown in FIG. 1) under the control of a processor control module (e.g., control module 42 shown in FIG. 1). The initial percussive pressure waveform shown in FIG. 2 may represent ineffective in-exsufflation therapy.

Figure 3:
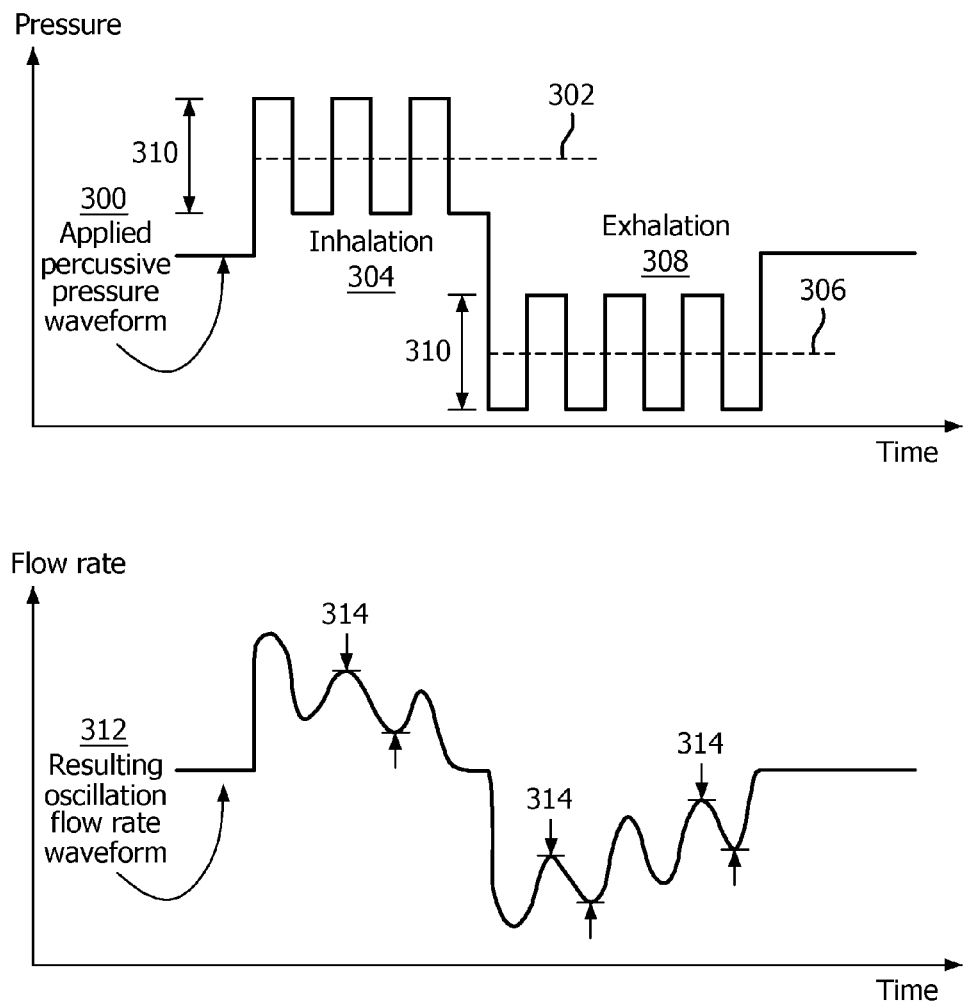
FIG. 3 shows another example of an applied percussive pressure waveform and the resulting oscillating flow rate waveform.

FIG. 3 shows another example of an applied percussive pressure waveform 300 and a resulting oscillating flow rate waveform 312. The percussive pressure waveform shown in FIG. 3 may represent effective in-exsufflation therapy. FIG. 3 may represent the in-exsufflation therapy percussive pressure waveform generated by a pressure generator (e.g., pressure generator 14 shown in FIG. 1) after adjustment by a processor adjustment module (e.g., adjustment module 46 shown in FIG. 1) responsive to a determination of ineffectiveness by a processor effectiveness module (e.g., effectiveness module 44 shown in FIG. 1). In the example shown in FIG. 3, the local median pressures, the amplitude, and the frequency are adjusted relative to FIG. 2. In FIG. 3 the applied percussive pressure waveform 300 has a local median pressure 302 of about 36 cm $H_2O$ during inhalation 304, a local median pressure 306 of about negative 36 cm $H_2O$ during exhalation 308, an amplitude 310 of 7.5 cm $H_2O$, and a frequency of 5 Hz. The resulting oscillating flow rate waveform 312 has a variable amplitude 314. Amplitude 314 of oscillating flow rate waveform 312 is larger relative to amplitude 214 shown in FIG. 2. According to the description provided above with respect to FIG. 1, the larger amplitude 314 of flow rate waveform 312 indicates that applied percussive waveform 300 is more effective than applied percussive waveform 200.

Returning to FIG. 1, in some embodiments, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 24, and/or other information that enables system 10 to function properly. Electronic storage 22 may be (in whole or in part) a separate component within system 10, or electronic storage 22 may be provided (in whole or in part) integrally with one or more other components of system 10 (e.g., pressure generator 14, processor 20, etc.). In some embodiments, information determined by processor 20 and stored by electronic storage 22 may comprise information related to previous respiration by subject 12, information related to previous in-exsufflation therapy on subject 12 by system 10, and/or other information.

User interface 24 is configured to provide an interface between system 10 and subject 12 through which subject 12 provides information to and receives information from system 10. This enables data, results, and/or instructions and any other communicable items, collectively referred to as "information," to be communicated between subject 12 and one or more of subject interface 16, processor 20, and/or other components of system 10. Examples of interface devices suitable for inclusion in user interface 24 include a keypad, buttons, switches, a keyboard, knobs, levers, a display screen, a touch screen, speakers, a microphone, a printer, and/or other interface devices. In some embodiments, user interface 24 includes a plurality of separate interfaces. It is to be understood that other communication techniques, either hard-wired or wireless, are also contemplated by the present disclosure as user interface 24. Other exemplary input devices and techniques adapted for use with system 10 as user interface 24 include, but are not limited to, an RS-232 port, RF link, an IR link, modem (telephone, cable or other). In short, any technique for communicating information with system 10 is contemplated by the present disclosure as user interface 24. By way of a non-limiting example, a user may enter a threshold value for the oscillating flow rate amplitude through user interface 24.

In some embodiments, information entered by a user through user interface 24 to system 10 may include, for example, designation of a therapy regime (e.g., inexsufflation, CPAP, etc.), in-exsufflation therapy initial percussive pressure waveform parameters, frequency range, an oscillating flow rate amplitude effectiveness threshold, and/or other information.

Figure 4:
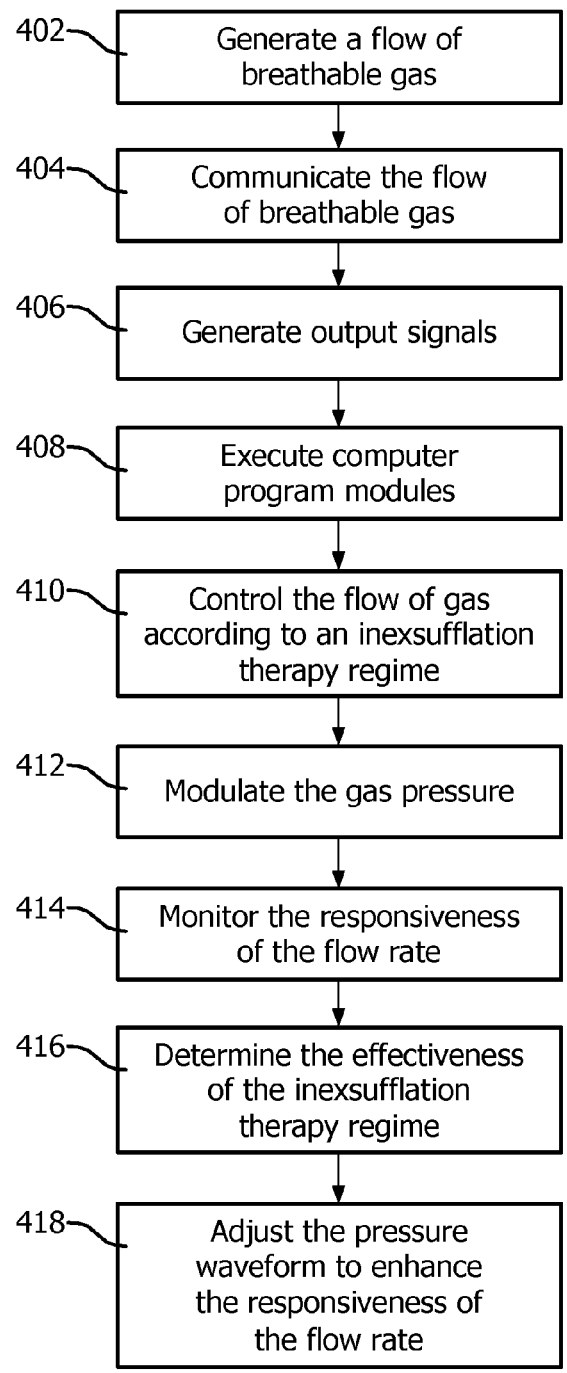
FIG. 4 illustrates a method to in-exsufflate a subject with an in-exsufflation system.

FIG. 4 illustrates a method 400 to in-exsufflate a subject with an in-exsufflation system. The system comprises a pressure generator, a subject interface, one or more sensors, and one or more processors. The processor comprises a control module, an effectiveness module, and an adjustment module. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, a pressurized flow of breathable gas is generated for delivery to an airway of a subject according to an in-exsufflation therapy regime. In some embodiments, operation 402 is performed by a pressure generator the same as or similar to pressure generator 14 (shown in FIG. 1 and described herein).

At an operation 404, the pressurized flow of breathable gas is communicated to the airway of the subject with a subject interface. In some embodiments, operation 404 is performed by a subject interface the same as or similar to subject interface 16 (shown in FIG. 1 and described herein).

At an operation 406, output signals conveying information related to one or more gas parameters of the flow of breathable gas are generated. In some embodiments, operation 406 is performed by sensors the same as or similar to sensors 18 (shown in FIG. 1 and described herein).

At an operation 408, computer program modules are executed. In some embodiments, operation 408 is performed by a processor the same as or similar to processor 20 (shown in FIG. 1 and describe herein).

At an operation 410, the pressure generator is controlled according to the in-exsufflation therapy regime. In some embodiments, operation 410 is performed by a processor module the same as or similar to control module 42 (shown in FIG. 1 and described herein).

At an operation 412, the pressure generator is caused to modulate a gas pressure within a respiratory phase between two or more pressure levels to generate a percussive pressure waveform during the respiratory phase. In some embodiments, operation 412 is performed by a processor module the same as or similar to control module 42 (shown in FIG. 1 and described herein).

At an operation 414, the responsiveness of a flow rate of the flow of breathable gas to the modulation in pressure during the respiratory phase is monitored. In some embodiments, operation 414 is performed by a processor module the same as or similar to control module 42 (shown in FIG. 1 and described herein).

At an operation 416, the effectiveness of the in-exsufflation therapy regime is determined. The determination of effectiveness is based on the responsiveness of the flow rate to the modulations in pressure. In some embodiments, operation 416 is performed by a processor module the same as or similar to effectiveness module 44 (shown in FIG. 1 and described herein).

At an operation 418, one or more parameters of the percussive pressure waveform are adjusted to enhance the responsiveness of the flow rate. In some embodiments, operation 418 is performed by a processor module the same as or similar to adjustment module 46 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to in-exsufflate a subject, the system comprising;
   (a) a pressure generator configured to generate a flow of breathable gas for delivery to an airway of the subject according to an in-exsufflation therapy regime;
   (b) a subject interface configured to place the pressure generator in fluid communication with the airway of the subject;
   (c) one or more sensors configured to generate one or more output signals conveying information related to one or more parameters of the flow of breathable gas; and
   (d) one or more processors configured to execute computer program modules, the computer program modules comprising:
      (1) a control module configured to control the pressure generator according to the in-exsufflation therapy regime, wherein controlling the pressure generator according to the in-exsufflation therapy regime comprises:
         (i) causing the pressure generator to modulate a gas pressure within a respiratory phase between two or more pressure levels to generate a percussive pressure waveform for delivery to the airway of the subject during the respiratory phase; and
         (ii) monitoring the responsiveness of a flow rate of the flow of breathable gas to the modulating of the gas pressure during the respiratory phase;
      (2) an effectiveness module configured to determine the effectiveness of the in-exsufflation therapy regime, the determination of effectiveness based on the responsiveness of the flow rate to the modulating of the gas pressure; and
      (3) an adjustment module configured to adjust one or more parameters of the percussive pressure waveform to enhance the responsiveness of the flow rate.

2. The system of claim 1, wherein the respiratory phase comprises inhalation or exhalation by the subject.

3. The system of claim 2, wherein the control module causes the pressure generator to generate the percussive pressure waveform with a first local median pressure during an inhalation of the subject, and a second local median pressure during an exhalation of the subject.

4. The system of claim 1, wherein adjustment comprises changing one or more of a first local median pressure during inhalation, a second local median pressure during exhalation, an amplitude, or a frequency of the percussive pressure waveform.

5. The system of claim 1, wherein greater responsiveness of the flow rate to the modulating of the gas pressure indicates greater effectiveness, and wherein an increase in an oscillating flow rate amplitude indicates greater responsiveness.

6. A method to generate an in-exsufflation pressure waveform for delivery to a subject with an in-exsufflation system, the system comprising a pressure generator, a subject interface, one or more sensors, and one or more processors, the one or more processors comprising a control module, an effectiveness module, and an adjustment module, the method comprising;
   generating a flow of breathable gas for delivery to an airway of the subject according to an in-exsufflation therapy regime with the pressure generator;
   communicating the flow of breathable gas to the airway of the subject with the subject interface;
   generating output signals conveying information related to one or more gas parameters of the flow of breathable gas with the one or more sensors;
   executing computer program modules with the processor;
   controlling the pressure generator according to the in-exsufflation therapy regime with the control module, wherein controlling the pressure generator according to the in-exsufflation therapy regime comprises:
  causing the pressure generator to modulate a gas pressure within a respiratory phase between two or more pressure levels to generate a percussive pressure waveform for delivery to the airway of the subject during the respiratory phase; and
  monitoring the responsiveness of a flow rate of the flow of breathable gas to the modulating of the gas pressure during the respiratory phase;
determining the effectiveness of the in-exsufflation therapy regime with the effectiveness module, the determination of effectiveness based on the responsiveness of the flow rate to the modulating of the gas pressure; and
adjusting one or more parameters of the percussive pressure waveform to enhance the responsiveness of the flow rate with the adjustment module.

7. The method of claim 6, wherein the respiratory phase comprises inhalation or exhalation by the subject.

8. The method of claim 7, further comprising causing the pressure generator to generate the percussive pressure waveform with a first local median pressure during an inhalation of the subject, and a second local median pressure during an exhalation of the subject.

9. The method of claim 6, wherein adjusting one or more parameters of the percussive pressure waveform comprises changing one or more of a first local median pressure during inhalation, a second local median pressure during exhalation, an amplitude, or a frequency of the percussive pressure waveform.

10. The method of claim 6, wherein greater responsiveness of the flow rate to the modulating of the gas pressure indicates greater effectiveness, and wherein an increase in an oscillating flow rate amplitude indicates greater responsiveness.

11. A system configured to in-exsufflate a subject, the system comprising;
  means for generating a flow of breathable gas for delivery to an airway of the subject according to an in-exsufflation therapy regime;
  means for communicating the flow of breathable gas to the airway of the subject;
  means for generating output signals conveying information related to one or more gas parameters of the flow of breathable gas;
  means for executing computer program modules;
  means for controlling the means for generating according to the in-exsufflation therapy regime, wherein controlling the means for generating according to the in-exsufflation therapy regime comprises:
    causing the means for generating according to the in-exsufflation therapy regime to modulate a gas pressure within a respiratory phase between two or more pressure levels to generate a percussive pressure waveform for delivery to the airway of the subject during the respiratory phase; and
    monitoring the responsiveness of a flow rate of the flow of breathable gas to the modulating of the gas pressure during the respiratory phase;
  means for determining the effectiveness of the in-exsufflation therapy regime, the determination of effectiveness based on the responsiveness of the flow rate to the modulating of the gas pressure; and
  means for adjusting one or more parameters of the percussive pressure waveform to enhance the responsiveness of the flow rate.

12. The system of claim 11, wherein the respiratory phase comprises inhalation or exhalation by the subject.

13. The system of claim 12, wherein the means for controlling the means for generating causes the means for generating to generate the percussive pressure waveform with a first local median pressure during an inhalation of the subject, and a second local median pressure during an exhalation of the subject.

14. The system of claim 11, wherein adjustment comprises changing one or more of a first local median pressure during inhalation, a second local median pressure during exhalation, an amplitude, or a frequency of the percussive pressure waveform.

15. The system of claim 11, wherein greater responsiveness of the flow rate to the modulating of the gas pressure indicates greater effectiveness, and wherein an increase in an oscillating flow rate amplitude indicates greater responsiveness.

* * * * *